United States Patent [19]

Muller et al.

[11] 4,150,131
[45] Apr. 17, 1979

[54] SUBSTITUTED OXADIAZOLOPYRIMIDINES

[75] Inventors: Jean-Claude Muller, Rixheim, France; Henri Ramuz, Birsfelden, Switzerland

[73] Assignee: Hoffmann-La Roche Inc., Nutley, N.J.

[21] Appl. No.: 873,183

[22] Filed: Jan. 27, 1978

[30] Foreign Application Priority Data

Feb. 4, 1977 [AT] Austria .................................... 745/77
Dec. 5, 1977 [LU] Luxembourg ........................... 78640

[51] Int. Cl.² ................... A61K 31/505; C07D 498/22
[52] U.S. Cl. ................... 424/251; 260/243.3; 544/255; 544/323
[58] Field of Search .................... 544/255; 424/251; 260/243.3

[56] References Cited

U.S. PATENT DOCUMENTS

| | | | |
|---|---|---|---|
| 3,769,288 | 10/1973 | Stahle et al. | 544/281 |
| 3,803,148 | 4/1974 | Gibbons | 544/255 |
| 3,816,422 | 6/1974 | Stahle et al. | 544/281 |
| 3,910,928 | 10/1975 | McCall et al. | 544/295 |

*Primary Examiner*—Paul M. Coughlan, Jr.
*Attorney, Agent, or Firm*—Jon S. Saxe; George M. Gould; William G. Isgro

[57] ABSTRACT

Oxadiazolopyrimidine derivatives of the formula

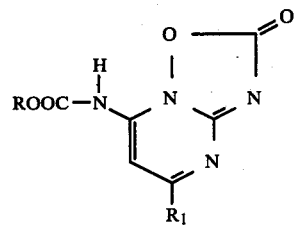

wherein R and $R_1$ are as hereinafter described, prepared, inter alia, by cyclizing a compound of the formula

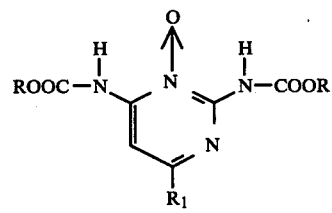

wherein R and $R_1$ are as hereinafter described.

The end products are useful in the treatment of vascular-conditioned hypertension or as vasodilators in the case of peripheral blood supply disorders.

18 Claims, No Drawings

SUBSTITUTED OXADIAZOLOPYRIMIDINES

BRIEF SUMMARY OF THE INVENTION

The invention relates to oxadiazolopyrimidines characterized by the formula

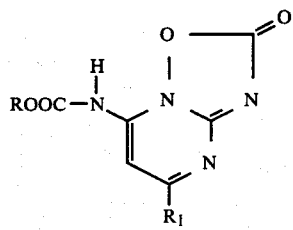

wherein R is alkyl, alkoxyalkyl, haloalkyl, aralkyl or aryl, and $R_1$ is dialkylamino, 4-alkyl-1,2,5,6-tetrahydropyridin-1-yl, piperidino, azabicyclononyl, azabicyclooctyl, 3-pyrrolin-1-yl, 3-hydroxy-1-piperidinyl or 4-hydroxy-1-piperidinyl or, when R is haloalkyl, aralkyl or aryl, $R_1$ can also be 1,2,5,6-tetrahydropyridin-1-yl, and salts thereof with pharmaceutically acceptable bases.

DETAILED DESCRIPTION OF THE INVENTION

The oxadiazolopyrimidine derivatives of the invention are characterized by the formula

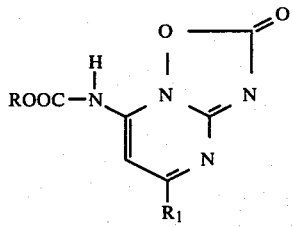

wherein R is alkyl, alkoxyalkyl, haloalkyl, aralkyl or aryl, and $R_1$ is dialkylamino, 4-alkyl-1,2,5,6-tetrahydropyridin-1-yl, piperidino, azabicyclononyl, azabicyclooctyl, 3-pyrrolin-1-yl, 3-hydroxy-1-piperidinyl or 4-hydroxy-1-piperidinyl, or when R is haloalkyl, aralkyl or aryl, $R_1$ can also be 1,2,5,6-tetrahydropyridin-1-yl, or a salt thereof with a pharmaceutically acceptable base.

The term "alkyl" used herein, alone or in combination, denotes straight-chain and branched-chain saturated hydrocarbon groups containing 1-8 carbon atoms such as, for example, methyl, ethyl, n-propyl, isopropyl, n-butyl, isobutyl, tert.-butyl and the like. The term "alkoxy" denotes alkyl ether groups in which the "alkyl" moiety is as earlier described. The term "haloalkyl" denotes alkyl groups in which one or more of the hydrogen atoms has been replaced by "halogen". The term "halogen" denotes fluorine, chlorine, bromine or iodine. The term "aryl" denotes a mononuclear or dinuclear aromatic group containing up to 12 carbon atoms in which one or more of the hydrogen atoms can be replaced by alkyl, alkoxy or halogen such as, for example, phenyl, halophenyl, methoxyphenyl, naphthyl and the like. The term "aralkyl" means an arylalkyl group such as benzyl, phenethyl and the like.

Preferred compounds of formula I are those in which R is alkyl, especially alkyl containing 1-4 carbon atoms. Furthermore, compounds of formula I wherein $R_1$ is piperidino or azabicyclononyl, preferably 3-azabicyclo[3.2.2]non-3-yl, are also preferred. Especially preferred are compounds of formula I wherein $R_1$ is piperidino.

From the foregoing it will be appreciated that those compounds of formula I wherein R is alkyl containing 1-4 carbon atoms and $R_1$ is piperidino or 3-azabicyclo[3.2.2]non-3-yl are especially preferred.

Especially preferred compounds of formula I are:

Methyl 5-piperidino-2-oxo-2H-[1,2,4]oxadiazolo[2,3-a]pyrimidine-7-carbamate;

Isobutyl 5-piperidino-2-oxo-2H-[1,2,4]oxadiazolo[2,3-a]pyrimidine-7-carbamate; and Butyl 5-piperidino-2-oxo-2H-[1,2,4]oxadiazolo[2,3-a]pyrimidine-7-carbamate.

According to the process of the invention, the oxadiazolopyrimidine derivatives (i.e., the compounds of formula I and their salts) can be prepared by (a) cyclizing a compound of the formula

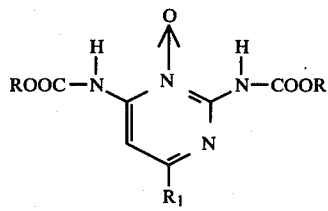

wherein R and $R_1$ are as previously described, or (b) trans-esterifying a compound of formula I with an alcohol of the formula

R'—OH wherein R' is alkyl, alkoxyalkyl, haloalkyl, aralkyl or aryl, but is different from R, to give a compound of the formula

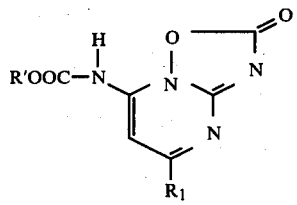

wherein R' is as previously described, and, if desired, (c) converting a resulting compound of formula I into a salt or converting a salt into a different salt.

The cyclization of a compound of formula II is carried out in a manner known per se by heating to a temperature in the range of from about 50° C. to about 200° C., preferably between about 100° C. and 150° C. The cyclization can be carried out in the absence or presence of a solvent or solvent mixture. If the cyclization is carried out in the presence of a solvent or solvent mixture, then there can be used as the solvent aromatic hydrocarbons such as benzene, toluene or xylene, chlorinated hydrocarbons such as chloroform, alcohols such as butanol or isobutanol, ethers such as dibutyl ether, dioxane or diethyleneglycol dimethyl ether, dimethylformamide, dimethylsulfoxide and the like or mixtures thereof.

It will be appreciated that there can either be used a solvent whose boiling point lies higher than the cyclization temperature, or that there can be used a solvent boiling in the temperature range mentioned earlier at its reflux temperature. The cyclization is preferably carried out using dimethylformamide or toluene as the solvent. The cyclization time depends on the temperature at which the cyclization is carried out and lies in the range of from about 0.25 hour to about 18 hours. If the cyclization is carried out at a temperature in the preferred temperature range of from about 100° C. to about 150° C., then the cyclization time is in the range of from about 0.25 hour to about 12 hours, preferably 0.25 hour to 2 hours. When an alcohol is used as the solvent, then it will be appreciated that, if a trans-esterification is to be avoided, the alcohol must yield a radical which corresponds to that present in the starting material utilized.

In another especially preferred embodiment, the cyclization is carried out in the presence of a base, in which case the temperature can be held subsantially lower. In this embodiment, the cyclization is preferably carried out at a temperature in the range of from about 0° C. to about 80° C., conveniently at room temperature. Suitable bases are inorganic bases, for example, alkali hydroxides such as sodium hydroxide and potassium hydroxide; alkaline earth hydroxides such as barium hydroxide and calcium hydroxide; carbonates such as potassium carbonate and sodium carbonate, and bicarbonates such as sodium bicarbonate; and organic bases such as dimethylamine, triethylamine, ethyldiisopropylamine and the like. When a base is used, the cyclization is carried out in a suitable inert solvent or solvent mixture. As the solvent there can be utilized a solvent referred to hereinbefore. When an inorganic base is used, the cyclization is conveniently carried out in a water-containing solvent mixture or in the presence of water in a two-phase system such as, for example, methylene chloride/water. When it is desired to bring about an intentional trans-esterification, the cyclization is preferably carried out in the presence of a base.

The trans-esterification of a compound of formula I is carried out in a known manner by reacting a compound of formula I with an appropriate alcohol at a temperature in the range of from about 25° C. to about 150° C. The trans-esterification is preferably carried out in the presence of a base. Suitable bases for this purpose are alkali alcoholates, alkali hydroxides, carbonates, and the like. It will be appreciated that when an alcoholate is used, this corresponds to the alcohol utilized. The trans-esterification is carried out in an inert organic solvent, for example, an aromatic hydrocarbon such as benzene or xylene, an ether such as dioxane, tetrahydrofuran or ethyleneglycol dimethyl ether, dimethylformamide, dimethylsulfoxide, and the like. If the alcohol used is liquid at the reaction temperature, then the excess alcohol can also serve as the reaction medium.

The starting materials of formula II are novel and also form part of the present invention. The compounds of formula II can be prepared, for example, by reacting a compound of formula III or a tautomer thereof of formula IV or V

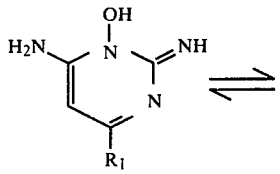

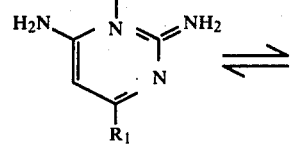

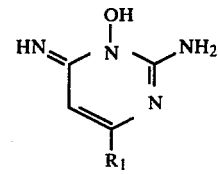

wherein $R_1$ is as previously described, with a chloroformic acid ester of the formula Cl-COOR      VI wherein R is as previously described.

The reaction of a compound of formula III or of a tautomer thereof of formula IV or V with a chloroformic acid ester of formula VI is carried out in an inert solvent or solvent mixture and in the presence of an acid binding agent. Suitable solvents for the present purpose are chlorinated hydrocarbons such as methylene chloride and chloroform, ethers such as diethyl ether, tetrahydrofuran and dioxane, dimethylformamide, and the like, or mixtures thereof. The reaction can also be carried out in a water-containing solvent or in the presence of water in a two-phase system such as, for example, methylene chloride/water. Examples of acid binding agents are bases such as triethylamine, ethyldiisopropylamine, dimethylamine, pyridine, alkali hydroxides and the like. When the reaction is carried out in the presence of a liquid base, then this can also serve as the solvent. The reaction is conveniently carried out at a temperature in the range of from about −10° C. to room temperature, preferably between about 0° C. and 10° C.

Alternatively, the starting materials of formula II can also be prepared by reacting a 6-chloro-2,4-pyrimidine-dicarbamate-3-oxide of the formula

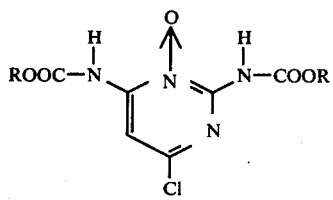

wherein R is as previously described, with an amine of the formula $R_1H$      VIII wherein $R_1$ is as previously described.

The reaction of a 6-chloro-2,4-pyrimidine-dicarbamate-3-oxide of formula VII with an amine of formula VIII is carried out in an inert solvent or solvent mixture. Suitable solvents for the present purpose are chlorinated hydrocarbons such as methylene chloride and chloroform, aromatic hydrocarbons such as toluene and xylene and the like or mixtures thereof. The reaction is preferably carried out under the atmosphere of an inert gas, preferably argon or nitrogen, at a temperature in the range of from about 0° C. to about 50° C., preferably at room temperature. In place of an inert solvent there can also be used an excess of amine of formula VIII. The starting materials of formula II wherein $R_1$ is 3-hydroxy-1-piperidinyl or 4-hydroxy-1-piperidinyl are preferably prepared according to this alternative procedure, because, in the case of processes starting from compounds of formula III or tautomers thereof of formulas IV and V, the hydroxy group may also be carbamoylated, which, of course, would reduce the yield of the desired starting material of formula II.

The compounds of formula III and their tautomers of formulas IV and V are known or can be prepared in analogy to the preparation of known compounds.

The compounds of formula VII are novel and can be prepared by reacting 2,4-diamino-6-chloropyrimidine-3-oxide of the formula

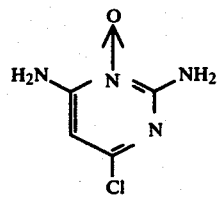

IX with a chloroformic acid ester of formula VI hereinbefore.

The reaction of 2,4-diamino-6-chloropyrimidine-3-oxide of formula IX with a chloroformic acid ester of formula VI is carried out under the conditions described hereinbefore for the reaction of a compound of formula III or a tautomer thereof of formula IV or V with a chloroformic acid ester of formula VI.

The compounds of formula I can be converted into salts, for example, by treatment with an inorganic base such as an alkali hydroxide, for example, sodium hydroxide or potassium hydroxide; an alkaline earth hydroxide for example, calcium hydroxide; or with an organic base, for example, a monoalkylamine such as methylamine, a dialkylamine such as dimethylamine, a trialkylamine such as triethylamine; a basic amino acid such as arginine; piperidine; an azabicyclooctane or -nonane, such as 3-azabicyclo[3.2.1]octane or 3-azabicyclo[3.2.2]nonane, or the like. Salts of the compounds of formula I can also be prepared by double-decomposition of a suitable salt. The pharmaceutically acceptable salts of the compounds of formula I are preferred.

The oxadiazolopyrimidine derivatives provided by the present invention possess long-lasting valuable vasodilating and/or blood pressure-lowering properties and can accordingly be used for the treatment of vascular-conditioned hypertensions and also as vasodilators in the case of peripheral blood supply disorders.

The blood pressure-lowering activity can be determined in conscious, spontaneous hypertensive rats by the following method:

The systolic blood pressure and the heart frequency are measured twice before administration of the test substance. The test substance is administered by means of an oesophageal probe twice daily, morning and afternoon. Both parameters are measured 1, 3, 6 and 24 hours after the administration and the percentage variations to the control values are calculated. The systolic blood pressure is measured indirectly in the tail artery of the rat by the method of Gerold et al. (Helv. Physiol. Acta 24: 58–69, 1966; Arzneimittelforschung 18: 1285–1287, 1968).

The results obtained are complied in the Table which follows. In each case, the maximum percentage deviation from the control values as well as the duration of activity in hours calculated as the average value from 5 experiments, are given.

| Compound | Dosage mg/kg p.o. | Blood pressure Δ % | Duration of activity in hours | Heart frequency Δ % | Duration of activity in hours |
|---|---|---|---|---|---|
| A | 3 | −26 | >24 | +15 | >24 |
|   | 10 | −35 | >24 | +20 | >24 |
| B | 1 | −11 | >24 | − 5 | >24 |
|   | 10 | −32 | >24 | +21 | >24 |
| C | 3 | −22 | >24 | −15 | >24 |
|   | 10 | −29 | >24 | +13 | >24 |
| D | 10 | −15 | >24 | +12 | 16 |
| E | 10 | − 8 | <24 | − 6 | <24 |
|   | 30 | −18 | >24 | +10 | 6 |

A = Ethyl 5-piperidino-2-oxo-2H-[1,2,4]oxadiazolo[2,3-a]-pyrimidine-7-carbamate
B = Isobutyl 5-piperidino-2-oxo-2H-[1,2,4]oxadiazolo[2,3-a]-pyridimine-7-carbamate
C = Butyl 5-piperidino-2-oxo-2H-[1,2,4]oxadiazolo[2,3-a]-pyrimidine-7-carbamate
D = Ethyl 5-[3-azabicyclo[3.2.2]non-3-yl]-2-oxo-2H-[1,2,4]-oxadiazolo[2,3-a]pyrimidine-7-carbamate
E = Benzyl 5-[3,6-dihydro-1(2H)-pyridyl]-2-oxo-2H-[1,2,4]-oxadiazolo[2,3-a]pyrimidine-7-carbamate The compounds of formula I and their pharmaceutically acceptable salts can be used as medicaments; for example, in the form of pharmaceutical preparations which contain them in association with a compatible pharmaceutical carrier material. The carrier material can be an organic or inorganic inert carrier material suitable for enteral or parenteral administration, for example, water, gelatin, gum arabic, lactose, starch, magnesium stearate, talc, vegetable oils, polyalkyleneglycols, or the like. The pharmaceutical preparations can be made up in solid form, for example, as tablets, dragees, suppositories or capsules, or in liquid form, for example, as solutions, suspensions or emulsions. The pharmaceutical preparations may be sterilized and/or may contain adjuvants such as preserving, stabilizing, wetting or emulsifying agents, salts for varying the osmotic pressure or buffers. The pharmaceutical preparations can also contain still other therapeutically valuable substances.

The daily dosage of a compound of formula I in the case of oral administration can comprise from about 10 to about 500 mg. and in the case of intravenous administration from about 1 to about 50 mg. It will be appreciated, however, that the aforementioned dosages are given by way of example only and can be varied according to the severity of the condition to be treated and according to the judgment of the person administering a compound of formula I.

The following Examples illustrate the process provided by the present invention. The melting points given in the Examples are not corrected.

EXAMPLE 1

Preparation of pure ethyl 5-piperidino-2-oxo-2H-[1,2,4]oxadiazolo[2,3-a]pyrimidine-7-carbamate 4.5 G. of diethyl 6-piperidino-2,4-pyrimidine-dicarbamate-3-oxide are treated under an argon atmosphere with 60 ml. of toluene and the mixture is heated to reflux for 12 hours. After cooling the mixture, the precipitate is filtered off and recrystallized from ether, there being obtained pure ethyl 5-piperidino-2-oxo-2H-[1,2,4]oxadiazolo[2,3-a]pyrimidine-7-carbamate, having a melting point of 209°-210° C. (decomposition).

In an analogous manner, from 4 g. of diisobutyl 6-piperidino-2,4-pyrimidine-dicarbamate-3-oxide, there was obtained isobutyl 5-piperidino-2-oxo-2H-[1,2,4]oxadiazolo[2,3-a]pyrimidine-7-carbamate, having a melting point of 188°-190° C.;

from 10.6 g. of dibutyl 6-piperidino-2,4-pyrimidine-dicarbamate-3-oxide, there was obtained butyl 5-piperidino-2-oxo-[1,2,4]oxadiazolo[2,3-a]pyrimidine-7-carbamate, having a melting point of 187°-190° C.; and from 12 g. of dibenzyl 6-[3,6-dihydro-1(2H)-pyridyl]-2,4-pyrimidine-dicarbamate-3-oxide, there was obtained benzyl 5-[3,6-dihydro-1(2H)-pyridyl]-2-oxo-2H-[1,2,4]oxadiazolo-[2,3-a]pyrimidine-7-carbamate, having a melting point of 218° C.

The diethyl 6-piperidino-2,4-pyrimidine-dicarbamate-3-oxide used as the starting material can be prepared as follows:

8 G. of 6-amino-1,2-dihydro-1-hydroxy-2-imino-4-piperidino-1-pyrimidine in 100 ml. of methylene chloride and 20 ml. of triethylamine are cooled to 5° C. while stirring. The mixture is treated with 20 ml. of chloroformic acid ethyl ester. The mixture is stirred at 5° C. for 30 minutes and then at room temperature for 18 hours. The mixture is extracted with 100 ml. of methylene chloride, washed with 50 ml. of water, dried over magnesium sulfate and evaporated under reduced pressure. Recrystallization of the residue from methylene chloride/ether yields diethyl 6-piperidino-2,4-pyrimidine-dicarbamate-3-oxide, having a melting point of 161°-162° C.

In an analogous manner, using chloroformic acid butyl ester, there is obtained dibutyl 6-piperidino-2,4-pyrimidine-dicarbamate-3-oxide, having a melting point of 187°-190° C.; and using chloroformic acid isobutyl ester there is obtained diisobutyl 6-piperidino-2,4-pyrimidine-dicarbamate-3-oxide, having a melting point of 138°-139° C.

The dibenzyl 6-[3,6-dihydro-1(2H)-pyridyl]-2,4-pyrimidine-dicarbamate-3-oxide likewise used as the starting material can be prepared as follows:

(A) 144.5 G. of 2,4-diamino-6-chloropyrimidine are suspended in 2000 ml. of ethanol. The suspension is warmed to 35° C. while stirring (about 15 minutes), the greater part of the material passing into solution. This mixture is then cooled down to 6°-8° C. and at this temperature there are added dropwise within 40 minutes 175 ml. of 40% peracetic acid in glacial acetic acid. After completion of the addition, the mixture is stirred at 6°-8° C. for a further 30 minutes. Thereafter, the mixture is left to warm up to room temperature, and stirred at this temperature for 3 hours. 2000 Ml. of petroleum ether are added, the mixture is stirred for 1 hour and then left to stand overnight. The separated precipitate is filtered off, back-washed with 200 ml. of petroleum ether and dried under reduced pressure, there being obtained 2,4-diamino-6-chloro-pyrimidine-3-oxide. Recrystallization yields analytically pure product having a melting point of 193° C.

(B) 75 G. of 2,4-diamino-6-chloropyrimidine are dissolved at 35° C. in 1500 ml. of ethanol. The solution is cooled to −10° C. and a solution of 100 g. of 3-chloroperbenzoic acid in 500 ml. of ethanol is slowly added dropwise within 1 hour. The suspension is subsequently stirred at −10° C. for 7 hours and left to stand at 5° C. overnight. The suspension is neutralized with 24 g. of sodium hydroxide in 100 ml. of water. The solid material is filtered off and recrystallized from ethanol, there being obtained pure 2,4-diamino-6-chloropyrimidine-3-oxide.

155 G. of 2,4-diamino-6-chloropyrimidine-3-oxide are mixed under an argon atmosphere with 640 ml. of o-xylene and 260 ml. of 1,2,5,6-tetrahydropyridine and the mixture is stirred. The mixture is then heated to reflux for 30 minutes, the internal temperature rising from 115° C. to 123° C. The mixture is then cooled to 5° C., treated with 40 g. of sodium hydroxide in 400 ml. of water and stirred at 5° C. for 1 hour. The precipitate formed is filtered off, washed with 200 ml. of water and recrystallized from 3000 ml. of water, there being obtained pure 2,4-diamino-6-[3,6-dihydro-1(2H)-pyridyl]pyrimidine-3-oxide, having a melting point of 263°-265° C. (decomposition).

20 G. of 2,4-diamino-6-[2,3-dihydro-1(2H)-pyridyl]-pyrimidine-3-oxide are suspended in 250 ml. of methylene chloride and 50 ml. of N-ethyldiisopropylamine and the mixture is cooled down to 5° C. 50 Ml. of chloroformic acid benzyl ester are added dropwise within 30 minutes and the mixture is then further stirred at room temperature for 15 hours. 200 Ml. of water are then added dropwise, the two phases are separated and the aqueous phase is extracted with methylene chloride. The organic phases are combined, dried over potassium carbonate and evaporated at 30° C. under reduced pressure. The residue is recrystallized from ether/ethanol, there being obtained dibenzyl 6-[3,6-dihydro-1(2H)-pyridyl]-2,4-pyrimidine-dicarbamate-3-oxide, having a melting point of 172° C.

EXAMPLE 2

Preparation of pure ethyl 5-dimethylamino-2-oxo-2H-[1,2,4]oxadiazolo[2,3-a]pyrimidine-7-carbamate 1 G. of diethyl 6-dimethylamino-2,4-pyrimidine-dicarbamate-3-oxide is heated to 140° C. for 30 minutes in 10 ml. of N,N-dimethylformamide under an argon atmosphere. The solution is cooled and the solvent is evaporated under reduced pressure. The crystalline residue is recrystallized from methylene chloride/ethanol, there being obtained pure ethyl 5-dimethylamino-2-oxo-2H-[1,2,4]oxadiazolo[2,3-a]pyrimidine-7-carbamate, having a melting point of 230°-240° C.

The diethyl 6-dimethylamino-2,4-pyrimidine-dicarbamate-3-oxide used as the starting material can be prepared as follows:

4 G. of 6-amino-1,2-dihydro-1-hydroxy-2-imino-4-dimethylamino-1-pyrimidine in 100 ml. of methylene chloride and 15 ml. of triethylamine are cooled to 5° C. while stirring. The mixture is treated with 10 ml. of chloroformic acid ethyl ester and stirred at room temperature for 16 hours. The mixture is subsequently extracted with 100 ml. of methylene chloride, washed with 60 ml. of water, dried over potassium carbonate and evaporated under reduced pressure. The residue is recrystallized from ether, there being obtained diethyl 6-dimethylamino-2,4-pyrimidine-dicarbamate-3-oxide, having a melting point of 237°–238° C.

EXAMPLE 3

Preparation of ethyl 5-{3-azabicyclo[3.2.2]non-3-yl}-2-oxo-2H-[1,2,4]oxadiazolo[2,3-a]pyrimidine-7-carbamate 4.1 G. of diethyl 6-{3-azabicyclo[3.2.2]non-3-yl}-2,4-pyrimidine-dicarbamate-3-oxide are suspended in 50 ml. of dimethylformamide and warmed to 140° C. for 30 minutes under an argon atmosphere. After cooling the solution, the dimethylformamide is distilled off under reduced pressure and the residue is filtered over silica gel. Elution with chloroform and ethanol yields ethyl 5-{3-azabicyclo[3.2.2]non-3-yl}-2-oxo-2H-[1,2,4]oxadiazolo[2,3-a]pyrimidine-7-carbamate, having a melting point of 210°–215° C. (decomposition). Analytically pure product is obtained by recrystallization from methylene chloride/ether.

The diethyl 6-{3-azabicyclo[3.2.2]non-3-yl}-2,4-pyrimidine-dicarbamate-3-oxide used as the starting material can be prepared as follows:

4 G. of 3-(2',4'-diamino-6'-pyrimidinyl)-3-azabicyclo[3.2.2]nonan-3'-oxide are cooled to 5° C. while stirring in 150 ml. of methylene chloride and 10 ml. of triethylamine. The mixture is then treated with 8 ml. of chloroformic acid ethyl ester, stirred at 5° C. for 30 minutes and subsequently at room temperature overnight. The solution is washed with 120 ml. of water, extracted with 200 ml. of methylene chloride, dried over potassium carbonate and evaporated under reduced pressure. Recrystallization of the residue from methylene chloride/ether yields diethyl 6-{3-azabicyclo[3.2.2]non-3-yl}-2,4-pyrimidine-dicarbamate-3-oxide, having a melting point of 158° C.

EXAMPLE 4

Preparation of (2-trichloroethyl) 5-[3,6-dihydro-1(2H)-pyridyl]-2-oxo-2H-[1,2,4]oxadiazolo[2,3-a]pyrimidine-7-carbamate 10 G. of bis(2-trichloroethyl) 6-[3,6-dihydro-1(2H)-pyridyl]-pyrimidine-dicarbamate-3-oxide are heated to 120° C. for 20 minutes under an argon atmosphere in 100 ml. of dimethylformamide. The solution is then evaporated under reduced pressure and the residue is chromatographed, there being obtained (2-trichloroethyl) 5-[3,6-dihydro-1(2H)-pyridyl]-2-oxo-2H-[1,2,4]oxadiazolo[2,3-a]pyrimidine-7-carbamate, having a melting point of 205°–207° L C. (decomposition).

The starting material can be prepared as follows:

10 G. of 2,4-diamino-6-[3,6-dihydro-1(2H)-pyridyl]-pyrimidine-3-oxide are suspended in 100 ml. of methylene chloride and 20 ml. of ethyldiisopropylamine. The suspension is cooled to 0° C. and, while stirring, there are added dropwise 20 ml. of chloroformic acid trichloroethyl ester. The mixture is then stirred at 5° C. for 3 hours. Subsequently, 100 ml. of water are cautiously added dropwise. The mixture is extracted with methylene chloride. The organic phases are dried over magnesium sulfate and the solvent is distilled off under reduced pressure. The residue is recrystallized from ethanol, there being obtained pure bis(2-trichloroethyl) 6-[3,6-dihydro-1(2H)-pyridyl]-2,4-pyrimidine-dicarbamate-3-oxide, having a melting point of 210° C. (decomposition).

EXAMPLE 5

Preparation of pure methyl 5-piperidino-2-oxo-2H-[1,2,4]oxadiazolo[2,3-a]pyrimidine-7-carbamate 5 G. of dimethyl 6-piperidino-2,4-pyrimidine-dicarbamate-3-oxide are dissolved in 200 ml. of methylene chloride and mixed with 100 ml. of water. While stirring vigorously, the mixture is adjusted with concentrated sodium hydroxide to pH 12.5 and stirred at this pH for 3 hours. The two phases are separated and the aqueous phase is adjusted to pH 4 with concentrated hydrochloric acid. The resulting white precipitate is filtered off, washed with water, pre-dried slightly and recrystallized from a mixture of methylene chloride and methanol, there being obtained pure methyl 5-piperidino-2-oxo-2H-[1,2,4]oxadiazolo[2,3-a]pyrimidine-7-carbamate, having a melting point of 210°–214° C. (decomposition).

The starting material can be prepared as follows:

56 G. of 2,4-diamino-6-chloropyrimidine-3-oxide in 500 ml. of dimethylformamide and 100 ml. of triethylamine are cooled to 0° C. 80 Ml. of chloroformic acid methyl ester are added dropwIse while stirring within 1 hour. After completion of the addition, the mixture is stirred for 48 hours. The precipitate is filtered off, suspended in a mixture of 2500 ml. of methylene chloride and 500 ml. of methanol and stirred for 80 minutes. The insoluble residue is filtered off and dried, there being obtained pure dimethyl 6-chloro-2,4-pyrimidine-dicarbamate-3-oxide, having a melting point of 204° C. (decomposition). The organic phase is washed with water and concentrated, there being obtained a further amount of pure material.

A suspension of 7.5 g. of dimethyl 6-chloro-2,4-pyrimidine-dicarbamate-3-oxide in 35 ml. of methylene chloride is treated with 14.5 ml. of piperidine and the mixture is stirred at room temperature under an argon atmosphere for 18 hours. The white precipitate formed is filtered off and recrystallized from a mixture of methylene chloride and methanol, there being obtained pure dimethyl 6-piperidino-2,4-pyrimidine-dicarbamate-3-oxide, having a melting point of 202° C. (decomposition).

EXAMPLE 6

Preparation of pure methyl 5-(3-pyrrolin-1-yl)-2-oxo-2H-[1,2,4]-oxadiazolo[2,3-a]pyrimidine-7-carbamate 4.5 G. of dimethyl 6-(3-pyrrolin-1-yl)-2,4-pyrimidine-dicarbamate-3-oxide are suspended in a mixture of 200 ml. of methylene chloride and 200 ml. of water. The suspension is adjusted with concentrated sodium hydroxide to pH 12.5 and stirred at this pH for 3 hours. The two phases are then separated and the aqueous phase is adjusted to pH 3 with concentrated hydrochloric acid. The separated white precipitate is filtered off, pre-dried and recrystallized from a mixture of methylene chloride and methanol, there being obtained pure methyl 5-(3-pyrrolin-1-yl)-2-oxo-2H-[1,2,4]-oxadiazolo[2,3-a]pyrimidine-7-carbamate, having a melting point of 230°–234° C. (decomposition).

The starting material can be prepared as follows:

A suspension of 12.5 g. of dimethyl 6-chloro-2,4-pyrimidine-dicarbamate-3-oxide in 100 ml. of methylene chloride is treated with 15 g. of 3-pyrroline and the mixture is stirred at room temperature under an argon atmosphere for 26 hours. The white precipitate formed is filtered off and recrystallized from a mixture of methylene chloride and methanol, there being obtained pure dimethyl 6-(3-pyrrolin-1-yl)-2,4-pyrimidine-dicarbamate-3-oxide, having a melting point of 206° C. (decomposition).

EXAMPLE 7

Preparation of pure methyl racemic-5-(4-hydroxy-1-piperidinyl)-2-oxo-2H-[1,2,4]-oxa-diazolo[2,3-a]pyrimidine-7-carbamate 3.1 G. of dimethyl racemic-6-(4-hydroxy-1-piperidinyl)-2,4-pyrimidine-dicarbamate-3-oxide are suspended in 100 ml. of methylene chloride and 100 ml. of water. The suspension is adjusted with concentrated sodium hydroxide to pH 12.6 and stirred at this pH for 3.5 hours. The two phases are then separated and the aqueous phase is adjusted to pH 3.2 with concentrated hydrochloric acid solution. The separated white precipitate is filtered off, pre-dried and recrystallized from methylene chloride and methanol, there being obtained pure methyl racemic-5-(4-hydroxy-1-piperidinyl)-2-oxo-2H-[1,2,4]-oxadiazolo[2,3-a]pyrimidine-7-carbamate, having a melting point of 250°–260° C. (decomposition).

The starting material can be prepared as follows:

A suspension of 2.5 g. of dimethyl 6-chloro-2,4-pyrimidine-dicarbamate-3-oxide in 100 ml. of methylene chloride is treated with 10 g. of 4-hydroxy-piperidine and stirred at room temperature under an argon atmosphere for 70 hours. The separated precipitate is filtered off and recrystallized from a mixture of methylene chloride and methanol, there being obtained pure dimethyl racemic-6-(4-hydroxy-1-piperidinyl)-2,4-pyrimidine-dicarbamate-3-oxide, having a melting point of 265°–266° C.

EXAMPLE 8

Preparation of pure methyl racemic-5-(3-hydroxy-1-piperidinyl)-2-oxo-2H-[1,2,4]oxadiazolo[2,3-a]pyrimidine-7-carbamate 5.6 G. of dimethyl racemic-6-(3-hydroxy-1-piperidinyl)-2,4-pyrimidine-dicarbamate-3-oxide are suspended in 100 ml. of methylene chloride and 100 ml. of water. The suspension is adjusted with concentrated sodium hydroxide to pH 12.7. The mixture is stirred for 1 hour, the two phases are then separated and the aqueous phase is adjusted to pH 3 with concentrated hydrochloric acid, a white precipitate separating out. This precipitate is filtered off and recrystallized from a mixture of methylene chloride and methanol, there being obtained pure methyl racemic-5-(3-hydroxy-1-piperidinyl)-2-oxo-2H-[1,2,4]oxadiazolo[2,3-a]pyrimidine-7-carbamate, having a melting point of 244°–247° C. (decomposition).

The starting material can be prepared as follows:

A suspension of 5.2 g. of dimethyl 6-chloro-2,4-pyrimidine-dicarbamate-3-oxide in 300 ml. of methylene chloride is treated with 12.4 g. of 3-hydroxy-piperidine and stirred for 60 hours under an argon atmosphere. The residue is then filtered off and the filtrate is concentrated, a white precipitate separating out. This precipitate is filtered off and recrystallized from a mixture of methylene chloride and methanol, there being obtained pure dimethyl racemic-6-(3-hydroxyl-1-piperidinyl)-2,4-pyrimidine-dicarbamate-3-oxide, having a melting point of 255° C. (decomposition).

The following Examples illustrate pharmaceutical preparations containing the oxadiazolopyrimidine derivatives provided by the present invention:

EXAMPLE A

Tablets containing the following ingredients are prepared:

|  |  |  |
|---|---|---|
| I | Butyl 5-piperidino-2-oxo-2H-[1,2,4]-oxa-diazolo[2,3-a]pyrimidine-7-carbamate (micronized) | 20.0 mg. |
|  | Lactose (powdered) | 40.0 mg. |
|  | Maize starch (white) | 24.9 mg. |
| II | Dioctyl sodium sulfosuccinate | 0.1 mg. |
|  | Maize starch (white) | 5.0 mg. |
|  | Water | q.s. |
| III | Maize starch (white) | 6.0 mg. |
| IV | Talc | 3.0 mg. |
|  | Magnesium stearate | 1.0 mg. |
|  |  | 100.0 mg. |

The ingredients of phase I are sieved and mixed. This mixture is moistened with the maize starch paste, phase II, and kneaded. The moist mass is granulated, dried and converted into a suitable granular size. Phase III is admixed. The resulting mixture is mixed with phase IV for a further short time. The ready-to-press mixture is pressed to tablets weighing 100 mg., having a diameter of 7 mm. and having a break-bar.

EXAMPLE B

Tablets containing the following ingredients are prepared:

|  |  |  |
|---|---|---|
| I | Butyl 5-piperidino-2-oxo-2H-[1,2,4] oxa-diazolo[2,3-a]pyrimidine-7-carbamate (micronized) | 200.0 mg. |
|  | Lactose (powdered) | 42.9 mg. |
|  | Maize starch (white) | 50.0 mg. |
| II | Dioctyl sodium sulfosuccinate | 0.1 mg. |
|  | Maize starch (white) | 20.0 mg. |
|  | Water | q.s. |
| III | Maize starch (white) | 30.0 mg. |
| IV | Talc | 3.5 mg. |
|  | Magnesium stearate | 3.5 mg. |
|  |  | 350.0 mg. |

The ingredients of phase I are sieved and mixed. This mixture is moistened with the maize starch paste, phase II, and kneaded. The moist mass is granulated, dried and converted into a suitable granular size. Phase III is admixed. The resulting mixture is mixed with phase IV for a further short time. The ready-to-press mixture is pressed to tablets weighing 350 mg., having a diameter of 11 mm and having a break bar.

EXAMPLE C

Capsules containing the following ingredients are prepared:

|  |  |  |
|---|---|---|
| I | Butyl 5-piperidino-2-oxo-2H-[1,2,4] oxa-diazolo[2,3-a] pyrimidine-7-carbamate (micronized) | 20.0 mg. |
|  | Lactose (powdered) | 48.0 mg. |
| II | Maize starch | 5.0 mg. |
|  | Water | q.s. |

-continued

| | | |
|---|---|---|
| III | Lactose (crystalline) | 50.0 mg. |
| | Maize starch | 15.0 mg. |
| IV | Talc | 10.0 mg. |
| | Magnesium stearate | 2.0 mg. |
| | | 150.0 mg. |

The ingredients of phase I are sieved and mixed. The mixture is moistened with the maize starch paste, phase II, and kneaded. The moist mass is granulated, dried and converted into a suitable granular size. Phase III is admixed. The resulting mixture is mixed with phase IV for a further short time. The mixture is filled into capsules (size 2) each containing 150 mg.

EXAMPLE D

Capsules containing the following ingredients are prepared:

| | | |
|---|---|---|
| I | Butyl 5-piperidino-2-oxo-2H-[1,2,4]-oxadiazolo[2,3-a]pyrimidine-7-carbamate (micronized) | 200.0 mg. |
| | Lactose (powdered) | 50.0 mg. |
| II | Maize starch | 15.0 mg. |
| | Water | q.s. |
| III | Lactose (crystalline) | 50.0 mg. |
| | Maize starch | 20.0 mg. |
| IV | Talc | 10.0 mg. |
| | Magnesium stearate | 5.0 mg. |
| | | 350.0 mg. |

The ingredients of phase I are sieved and mixed. The mixture is moistened with the maize starch paste, phase II, and kneaded. The moist mass is granulated, dried and converted into a suitable granular size. Phase III is admixed. The resulting mixture is mixed with phase IV for a further short time. The mixture is filled into capsules (size 1) each containing 350 mg.

EXAMPLE E

An aqueous drop suspension containing the following ingredients is prepared:

| | 10 mg. per 1 ml. |
|---|---|
| Butyl 5-piperidino-2-oxo-2H-[1,2,4]oxadiazolo-[2,3-a]pyrimidine-7-carbamate (micronized) | 0.1 g. |
| Sodium benzoate | 0.035 g. |
| Sodium saccharin | 0.015 g. |
| Acrylic acid polymerizate | 01 – 1.0 g. |
| Saccharose | 3.5 g. |
| Citric acid | 0.025 g. |
| Polyoxyethylene stearate | 0.002 – 0.01 g. |
| Sodium hydroxide | q.s. |
| Aroma | q.s. |
| Foodstuff colorant | q.s. |
| Deionized water | ad 10.0 ml. |

EXAMPLE F

An aqueous drop suspension containing the following ingredients is prepared:

| | 100 mg.per 1 ml. |
|---|---|
| Butyl 5-piperidino-2-oxo-2H-[1,2,4]oxadiazolo[2,3-a]-pyrimidine-7-carbamate (micronized) | 1.0 g. |
| Sodium benzoate | 0.035 g. |
| Sodium saccharin | 0.015 g. |
| Acrylic acid polymerizate | 0.05–0.5 g. |
| Saccharose | 3.5 g. |
| Citric acid | 0.025 g. |
| Polyoxyethylene stearate | 0.002–0.01 g. |
| Sodium hydroxide | q.s. |
| Aroma | q.s. |
| Foodstuff colorant | q.s. |
| Deionized water | ad 10.0 ml. |

We claim:

1. A compound of the formula $$ROOC-N(H)-\text{[oxadiazolopyrimidine ring with } R_1\text{]} \quad \quad I$$

wherein R is alkyl, alkoxyalkyl, haloalkyl, aralkyl or aryl, and $R_1$ is dialkylamino, 4-alkyl-1,2,5,6-tetrahydropyridin-1-yl, piperidino, azabicyclononyl, azabicyclooctyl, 3-pyrrolin-1-yl, 3-hydroxy-1-piperidinyl or 4-hydroxy-1-piperidinyl or, when R is haloalkyl, aralkyl or aryl, $R_1$ can also be 1,2,5,6-tetrahydropyridin-1-yl, or a salt thereof with a pharmaceutically acceptable base.

2. A compound in accordance with claim 1, wherein R is alkyl, alkoxyalkyl, haloalkyl, aralkyl or aryl, and $R_1$ is dialkylamino, 4-alkyl-1,2,5,6-tetrahydropyridin-1-yl, piperidino, azabicyclononyl or azabicyclooctyl or, when R is haloalkyl, aralkyl or aryl, $R_1$ can also be 1,2,5,6-tetrahydropyridin-1-yl.

3. A compound in accordance with claim 2, wherein R is alkyl.

4. A compound in accordance with claim 3, wherein R is alkyl of 1–4 carbon atoms.

5. A compound in accordance with claim 2, wherein R is piperidino or azabicyclononyl.

6. A compound in accordance with claim 1, wherein R is alkyl of 1–4 carbon atoms and $R_1$ is 1-piperidino or 3-azabicyclo[3.2.2]nonyl.

7. A compound in accordance with claim 1, ethyl 5-piperidino-2-oxo-2H-[1,2,4]-oxadiazolo[2,3-a]pyrimidine-7-carbamate.

8. A compound in accordance with claim 1, isobutyl 5-piperidino-2-oxo-2H-[1,2,4]oxadiazolo[2,3-a]pyrimidine-7-carbamate.

9. A compound in accordance with claim 1, butyl 5-piperidino-2-oxo-2H-[1,2,4]oxadiazolo[2,3-a]pyrimidine-7-carbamate.

10. A compound in accordance with claim 1, ethyl 5-{3-azabicyclo[3.2.2]non-3-yl}-2-oxo-2H-[1,2,4]oxadiazolo[2,3-a]pyrimidine-7-carbamate.

11. A compound in accordance with claim 1, benzyl 5-[3,6-dihydro-1(2H)-pyridyl]-2-oxo-2H-[1,2,4]oxadiazolo[2,3-a]pyrimidine-7-carbamate.

12. A compound in accordance with claim 1, ethyl 5-dimethylamino-2-oxo-2H-[1,2,4]oxadiazolo[2,3-a]pyrimidine-7-carbamate.

13. A compound in accordance with claim 1, (2-trichloroethyl) 5-[3,6-dihydro-1(2H)-pyridyl]-2-oxo-2H-[1,2,4]oxadiazolo[2,3-a]pyrimidine-7-carbamate.

14. A compound in accordance with claim 1, methyl 5-piperidino-2-oxo-2H-[1,2,4]oxadiazolo[2,3-a]pyrimidine-7-carbamate.

15. A compound in accordance with claim 1, methyl 5-(3-pyrrolin-1-yl)-2-oxo-2H-[1,2,4]oxadiazolo[2,3-a]pyrimidine-7-carbamate.

16. A compound in accordance with claim 1, methyl racemic-5-(4-hydroxy-1-piperidinyl)-2-oxo-2H-[1,2,4oxadiazolo[2,3-a]pyrimidine-7-carbamate.

17. A compound in accordance with claim 1, methyl racemic-5-(3-hydroxy-1-piperidinyl)-2-oxo-2H-[1,2,4]oxadiazolo[2,3]-a]pyrimidine-7-carbamate.

18. A pharmaceutical composition comprising a compound of the formula

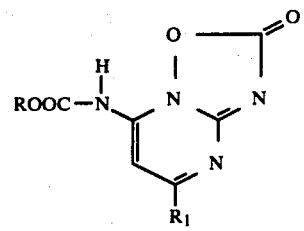

wherein R is alkyl, alkoxyalkyl, haloalkyl, aralkyl or aryl, and $R_1$ is dialkylamino, 4-alkyl-1,2,5,6-tetrahydropyridin-1-yl, piperidino, azabicyclononyl, azabicyclooctyl, 3-pyrrolin-1-yl, 3-hydroxy-1-piperidinyl or 4-hydroxy-1-piperidinyl, or when R is haloalkyl, aralkyl or aryl, $R_1$ can also be 1,2,5,6-tetrahydropyridin-1-yl, or a salt thereof with a pharmaceutically acceptable base and a compatible pharmaceutical carrier material.

* * * * *

UNITED STATES PATENT AND TRADEMARK OFFICE
CERTIFICATE OF CORRECTION

PATENT NO. : 4,150,131
DATED : April 17, 1979
INVENTOR(S) : Muller et al.

It is certified that error appears in the above-identified patent and that said Letters Patent are hereby corrected as shown below:

Column 15, claim 15, line 14, "[1,2,4oxadiazolo" should be:

[1,2,4] oxadiazolo

Column 15, claim 17, line 17, "[2,3]-a] pyrimidine-" should be:

[2,3-a] pyrimidine

Signed and Sealed this

Eleventh Day of September 1979

[SEAL]

Attest:

LUTRELLE F. PARKER
Attesting Officer   Acting Commissioner of Patents and Trademarks